United States Patent [19]

Manning

[11] Patent Number: 5,066,348

[45] Date of Patent: Nov. 19, 1991

[54] METHOD OF MAKING A FLANNELIZED FILM

[75] Inventor: James H. Manning, Neenah, Wis.

[73] Assignee: James River Corporation, Richmond, Va.

[21] Appl. No.: 445,028

[22] Filed: Dec. 4, 1989

[51] Int. Cl.$^5$ .............................................. B32B 31/08
[52] U.S. Cl. ..................................... 156/164; 156/254
[58] Field of Search ................ 156/254, 164; 428/91, 428/511, 513; 604/383

[56] References Cited

U.S. PATENT DOCUMENTS

| | | | |
|---|---|---|---|
| 1,758,502 | 5/1930 | Crowell | 156/254 |
| 2,768,902 | 10/1956 | Scholl. | |
| 3,062,675 | 11/1962 | Sheiffo. | |
| 3,121,657 | 2/1964 | Magill. | |
| 3,174,889 | 3/1965 | Anderson et al. . | |
| 3,607,348 | 9/1971 | Wray et al. . | |
| 3,765,999 | 10/1973 | Toyoda. | |
| 3,824,116 | 7/1974 | Anderson et al. . | |
| 3,837,946 | 9/1974 | Gribbin. | |
| 3,837,995 | 9/1974 | Floden. | |
| 3,916,447 | 11/1975 | Thompson. | |
| 3,967,623 | 7/1976 | Butterworth et al. | 604/383 X |
| 4,347,844 | 9/1982 | Ohki et al. . | |
| 4,394,416 | 7/1983 | Shimizu et al. | 152/254 X |
| 4,409,049 | 10/1983 | Passafiume et al. | 156/164 |

OTHER PUBLICATIONS

"Units of Measurements and Conversion Factors", TAPPI; 1989; pp. 1 and 2.

*Primary Examiner*—Michael W. Ball
*Assistant Examiner*—Nancy T. Krawczyk
*Attorney, Agent, or Firm*—Finnegan, Henderson, Farabow, Garrett & Dunner

[57] ABSTRACT

A flannelized film and a method of making a flannelized film are disclosed. Layers of plastic film are fed between two rollers meeting at a nip, the contiguous surfaces of the layers being coated with an adhesive or comprising a heat-softened coextruded layer. A layer of creped tissue comprising cellulosic fibers is laminated between the contiguous surfaces of the layers of plastic film to form an intermediate laminate structure. The cellulosic fibers of the intermediate laminate structure are split at the exit side of the nip such that a portion of the cellulosic fibers is adhered to each plastic layer and has components extending in a direction substantially perpendicular with respect to the plane of the plastic film. This gives the plastic film the look and feel of flannel for improving the aesthetics of disposable absorbent products such as diapers, feminine napkins and underpads.

6 Claims, 2 Drawing Sheets

METHOD OF MAKING A FLANNELIZED FILM

BACKGROUND OF THE INVENTION

A. Field of the Invention

The present invention relates to a flannelized film having a cloth-like texture and a method of making a flannelized film.

B. Description of the Prior Art

Plastic films are used extensively in the paper products industry as a barrier layer in disposable absorbent products. Such products include diapers, feminine napkins, underpads and tablecloths. However, the plastic film used in these products has unattractive aesthetics. The plastic film retains a plastic look and feel, which is especially undesirable for those products which are worn close to the body, such as diapers, feminine napkins and underpads.

In order to overcome this drawback, plastic films are usually embossed to give them a more cloth-like look and feel. However, even embossing the plastic film fails to completely overcome this drawback, as the plastic film still retains a plastic look and feel.

SUMMARY OF THE INVENTION

Accordingly, it is an object of this invention to provide a flannelized film and a method of making a flannelized film that overcomes the problems and disadvantages of the above discussed prior art.

It is a further object of the invention to provide a flannelized film and a method of making a flannelized film having a cloth-like texture.

It is still a further object of this invention to provide a flannelized film that can be produced by simple lamination techniques which provide a flannelized film that is inexpensive to manufacture.

Additional advantages of the invention will be set forth in part in the description which follows, and in part will be obvious from the description, or may be learned by practice of the invention. The advantages of the invention will be realized and attained by means of the elements and combinations particularly pointed out in the appended claims.

To achieve the objects and purposes of the invention, in accordance with a first embodiment of the invention there is provided a method of making a flannelized film having a cloth-like texture comprising: feeding a plurality of layers of plastic film between a plurality of rollers, the rollers meeting at a nip having a feed side and an exit side; adhering an adhesive onto one surface of each layer of plastic film before the layers of plastic film reach the nip; laminating a layer of creped tissue comprising a plurality of cellulosic fibers between the layers of plastic film, the layer of creped tissue coming into contact with the surface of the plastic film having adhered adhesive to form an intermediate laminate structure; splitting the fibers of the creped tissue layer of the intermediate laminate structure such that a portion of the split fibers has components extending in a substantially perpendicular direction with respect to the plane of the plastic film; and feeding the split intermediate laminate structure from the exit side of the nip to a plurality of take-up rollers.

Preferably, the fibers of the creped tissue layer are split along the nominal plane of the layer of creped tissue to form a plurality of generally U-shaped members.

The flannelized film having a cloth-like texture produced according to the method of the first embodiment of the present invention comprises: a layer of plastic film; a layer of adhesive adhered to the plastic film; and a portion of a split layer of creped tissue laminated onto the surface of the plastic film having adhered adhesive, the portion of the split layer of creped tissue comprising a plurality of cellulosic fibers having components extending in a substantially perpendicular direction with respect to the plane of the plastic film.

Preferably, the portion of the split layer of creped tissue comprises a plurality of generally U-shaped members.

In accordance with a second embodiment of the present invention there is provided a method of making a flannelized film having a cloth-like texture comprising: feeding a plurality of layers of co-extruded plastic film comprising a relatively thick layer and a relatively thin layer having a lower melting temperature than that of the relatively thick layer between a plurality of heated rollers, the rollers meeting at a nip having a feed side and an exit side; preheating the layers of plastic film to the softening point of the thin layer before the layers of plastic film reach the nip; laminating a layer of creped tissue comprising a plurality of cellulosic fibers between the plurality of layers of plastic film, the layer of creped tissue coming into contact with the surface of the preheated plastic film to form an intermediate laminate structure; splitting the fibers of the creped tissue layer of the intermediate laminate structure such that a portion of the split fibers has components extending in a substantially perpendicular direction with respect to the plane of the plastic film; and feeding the split intermediate laminate structure to a plurality of take-up rollers.

Preferably, the fibers of the layer of creped tissue are split along the nominal plane of the layer of creped tissue to form a plurality of U-shaped members.

The flannelized film having a cloth-like texture produced according to the method of the second embodiment of the present invention comprises: a layer of co-extruded plastic film including a relatively thick layer and a relatively thin layer having a lower melting temperature than that of the thick layer; and a portion of a split layer of creped tissue laminated onto the surface of the relatively thin layer of the co-extruded plastic film, the portion of the split layer of the creped tissue comprising a plurality of cellulosic fibers having components extending in a substantially perpendicular direction with respect to the plane of the plastic film.

Preferably, the portion of the split layer of creped tissue comprises a plurality of generally U-shaped members.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
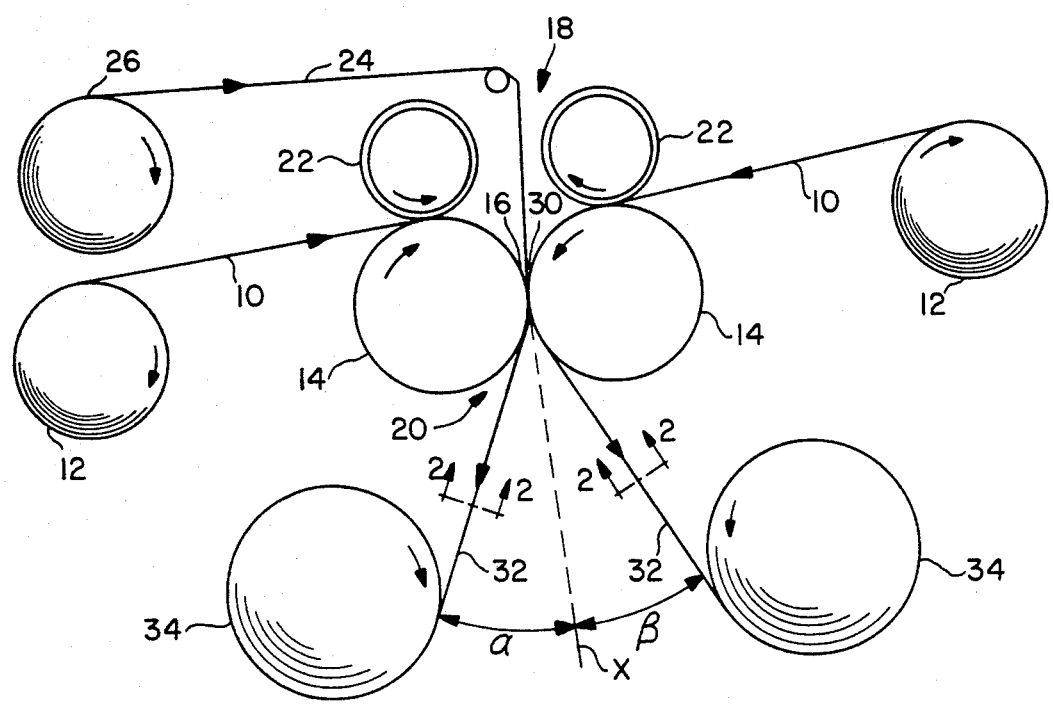
FIG. 1 is a schematic diagram of a method of making a flannelized plastic film according to a first embodiment of the present invention.

Reference will now be made in detail to the present preferred embodiments of the invention, examples of which are illustrated in the accompanying drawings. Wherever possible, the same reference numbers will be used throughout the drawings to refer to the same or like parts.

In accordance with a first embodiment of the invention, there is provided a method of making a flannelized film having a cloth-like texture. The method and the resultant film are described in conjunction with FIGS. 1 and 2. The method first comprises the step of feeding a plurality of layers of plastic film, shown at 10 in FIG. 1, from a pair of feed rollers 12 between a pair of rollers 14. Rollers 14 are preferably made of steel and meet at a nip 16 having a feed side and an exit side shown generally at 18 and 20, respectively. An adhesive applied by a pair of feed rollers 22 is adhered onto one surface of each layer 10 of plastic film before the layers reach nip 16.

As embodied herein, the adhesive preferably comprises a hot-melt adhesive. The hot-melt adhesive may be applied to the layers of plastic film by various techniques. For example, the hot-melt adhesive may be printed onto the layers of plastic film in a pattern or onto the entire surface of the layers. Alternatively, the hot-melt adhesive may be sprayed or pressed onto the layers of plastic film.

A layer 24 of creped tissue is fed from a feed roller 26 into nip 16 of rollers 14 and is laminated between layers 10 of the plastic film. The creped tissue comprises a plurality of cellulosic fibers. Preferably, the fibers extend on each side of the nominal plane of layer 24 of creped tissue in a substantially sinusoidal manner. Layer 24 of creped tissue comes into contact at nip 16 with the surface of layer 10 of plastic film having adhered adhesive to form an intermediate laminate structure 30.

The fibers of layer 24 of creped tissue of the intermediate laminate structure 30 are then split as the intermediate laminate structure leaves exit side 20 of nip 16. Specifically, intermediate laminate structure 30 is peeled at an optimal peeling speed, in such a manner that angles a and B of the peeling directions with respect to a central peeling line X as shown in FIG. 1 are equal to each other. As a result, the tearing stress is concentrated substantially on the nominal plane of creped tissue layer 24, and creped tissue layer 24 is evenly split along the nominal plane. Intermediate laminate structure 30 is thereby divided into two equal parts, forming flannelized film 32 which is fed to a pair of take-up rollers 34.

Figure 2:
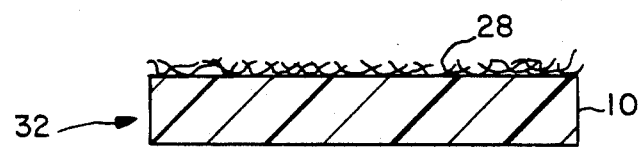
FIG. 2 is a sectional view along line 2—2 of FIG. 1 of the flannelized plastic film produced by the method described with respect to FIG. 1.

Intermediate laminate structure 30 is split such that a portion of the split fibers has components which extend in a substantially perpendicular direction with respect to the plane of the plastic film. It is this orientation of the split fibers which gives film 32 the look and feel of flannel. Preferably, the fibers of creped tissue layer 24 are split along the nominal plane of the layer 24 to form a plurality of generally U-shaped members 28 as best seen in FIG. 2. Members 28 may be irregular in shape and distribution as shown in FIG. 2.

It is important that the bond strength between the plastic film layer and the creped tissue layer is higher than the strength at which the intermediate laminate structure splits. If the bond strength between the plastic film layer and the creped tissue layer is lower than the strength at which the intermediate laminate structure splits, the splitting is not caused by the above-described peeling operation. Rather, the bonded creped tissue layer is merely separated from the plastic film layer and no split intermediate laminate structure is obtained.

Flannelized film 32 produced by the above-described method is shown in FIG. 2. Flannelized film 32 includes layer 10 of plastic film and a layer of adhesive (not shown in FIG. 2) adhered to the layer of plastic film as described above. A portion of a split layer of creped tissue is laminated onto the surface of the plastic film having adhesive thereon. Preferably, the fibers of the layer of creped tissue are split to form generally U-shaped members 28 as described above. The split layer of creped tissue comprises a plurality of split cellulosic fibers having components which extend in a substantially perpendicular direction with respect to the plane of the film. The orientation of these members gives film 32 the look and feel of flannel.

Figure 3:
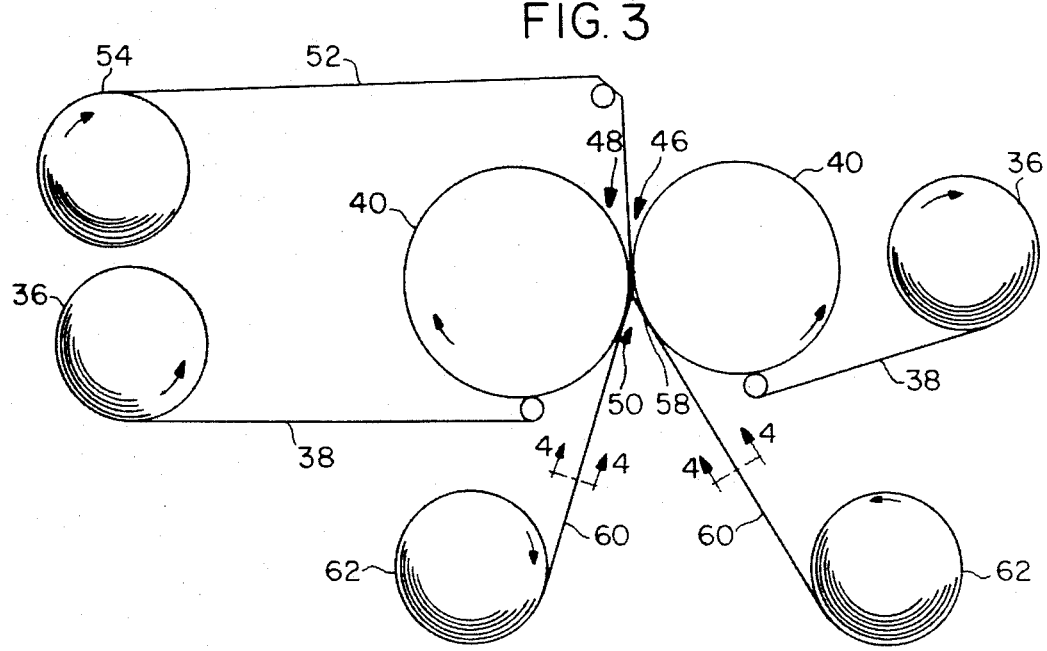
FIG. 3 is a schematic diagram of a method of making a flannelized plastic film according to a second embodiment of the present invention.
Figure 4:
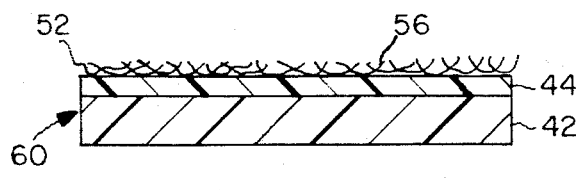
FIG. 4 is a sectional view along line 4—4 of FIG. 3 of the flannelized plastic film produced by the method described with respect to FIG. 3.

In accordance with a second embodiment of the present invention, an alternative method of making a flannelized film having a cloth-like texture and the resultant flannelized film are described in conjunction with FIGS. 3 and 4. The method comprises feeding, from a pair of feed rollers 36, a plurality of layers 38 of co-extruded plastic film between a pair of heated rollers 40. Each layer 38 of plastic film comprises a relatively thick and a relatively thin layer of plastic film 42 and 44, respectively, as shown in FIG. 4. Rollers 40 meet at a nip 46 having a feed side and an exit side, 48 and 50, respectively. Relatively thin layer 44 has a lower melting temperature than that of relatively thick layer 42. Rollers 40 are preferably made of steel and are heated such that layer 38 of co-extruded plastic film is preheated to the softening point of thin layer 44 before reaching nip 46.

The method in accordance with the second embodiment of the invention further comprises the step of laminating a layer 52 of creped tissue fed from a feed roll 54 between layers 38 of co-extruded plastic film. Layer 52 comprises a plurality of cellulosic fibers. Preferably, the fibers extend on each side of the nominal plane of layer 52 of creped tissue in a substantially sinusoidal manner. The creped tissue comes into contact with the surface of preheated layer 38 at nip 46 to form an intermediate laminate structure 58.

The fibers of the layer of creped tissue of intermediate laminate structure 58 are then split as the intermediate laminate structure exits from exit side 50 of nip 46. When delamination is carried out between plastic film and layer 52 of creped tissue in the above-described manner, the fibers of layer 52 are split and flannelized film 60 is obtained. Film 60 is fed to a pair of take-up rollers 62.

By splitting intermediate laminate structure 58, a portion of the split fibers of the creped tissue have components which extend in a substantially perpendicular direction with respect to the plane of the plastic film. It is this orientation of the split fibers which gives the plastic the look and feel of flannel for much improved aesthetics. Preferably, the fibers of creped tissue layer 52 are split along the nominal plane of layer 52 to form a plurality of generally U-shaped members 56 as best seen in FIG. 4. Members 56 may be irregular in shape and distribution as shown in FIG. 4.

Flannelized film 60 produced according to the above-described method of the second embodiment of the present invention is shown in FIG. 4. Flannelized film 60 comprises a co-extruded plastic film layer, including relatively thick layer 42 and relatively thin layer 44 having a lower melting temperature than that of the thick layer as described above.

Flannelized film 60 also includes a split layer of creped tissue which has been laminated onto the surface relatively thin layer 44 of the co-extruded plastic film. Preferably, the fibers of the creped tissue are split to form generally U-shaped members 56, as described above. The split layer of the creped tissue comprises a plurality of fibers having components which extend in a substantially perpendicular direction with respect to the plane of the plastic film. The orientation of these members gives film 60 the look and feel of flannel.

Figure 5:
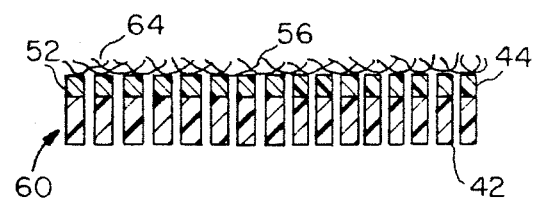
FIG. 5 is a variation of the flannelized plastic film shown in FIG. 4 and made according to the method shown in FIG. 3.

FIG. 5 shows a modification of the flannelized film shown in FIG. 4. Apertures 64 as shown in FIG. 5 are formed in flannelized film 60 and extend completely therethrough. The apertured flannelized film structure may be used as the cover layer on disposable sanitary absorbent diapers and feminine napkins. Although shown as a modification of the second embodiment (FIGS. 3 and 4), such modification may be made to the flannelized film produced in accordance with the first embodiment (FIGS. 1 and 2) of the present invention without departing from the scope and spirit of the general inventive concept.

It will be apparent to those skilled in the art that various modifications and variations can be made in the present invention without departing from the scope or spirit of the invention. For example, the layer of plastic film used in accordance with the first and second embodiments of the present invention can be a thin-gauge plastic having a thickness in the range of ½ to 2 mils. The plastic film may comprise a variety of plastics including, for example, polyethylene, polypropylene, polyvinyl chloride, polyester or nylon. Alternatively, the layer of plastic film may comprise a micro-porous membrane consisting of either polytetrafluoroethylene, e.g., expanded polytetrafluoroethylene, commonly sold under the trademark Goretex TM, or polypropylene, commonly sold under the trademark Celgard TM. By way of further example, the plastic film may be a filled film containing a filler such as kaolin, as disclosed in U.S. Pat. No. 4,347,844, or Kimdura TM, as disclosed in U.S. Pat. No. 3,765,999.

The creped tissue layer of the first and second embodiments is preferably produced from a dry web of cellulosic fibers such as wood pulp by conventional lamination or hot-melt lamination techniques. The creped tissue has a basis in the rang of weight of 5 to 20 lb/ream and preferably 10 lb/ream, prior to the splitting step. A value of less than 5 lb/ream causes the adhesive or the softened plastic film to bleed through the creped tissue layer, making it impossible to split the intermediate laminate structure. A value greater than 20 lb/ream produces a flannelized film having fibers which are loosely adhered to the surface of the film and which are easily rubbed away.

Figure 6:
FIG. 6 is an enlarged photograph of the cellulosic fibers of the creped tissue layer produced in accordance with the first enbodiment of the present invention shown in FIGS. 1 and 2.

FIG. 6 is a micro-photograph of the flannelized film produced in accordance with the first embodiment of the present invention discussed above with respect to FIGS. 1 and 2. The film as shown in FIG. 6 has been laminated with a layer of creped tissue comprising wood pulp which has a basis weight of 10 lb/ream prior to the splitting step. Since the tissue layer is evenly split along the nominal plane of the creped tissue layer, the creped tissue layer shown in FIG. 6 has a basis weight of 5 lb/ream.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a flannelized film having a flannel cloth-like texture comprising:

feeding a plurality of layers of plastic film between a plurality of rollers, the rollers meeting at a nip having a feed side and an exit side;

adhering an adhesive onto one surface of each layer of plastic film before the layers of plastic film reach the nip;

laminating a layer of creped tissue comprising a plurality of sinusoidal cellulosic fibers defining a nominal plane between the layers of plastic film, the sinusoidal fibers of said layer of creped tissue coming into contact with the surface of the plastic film having adhered adhesive to form an intermediate laminate structure;

splitting the intermediate laminate structure along the nominal plane of the creped tissue such that said sinusoidal fibers are split into a plurality of U-shaped fibers, a portion of the U-shaped fibers having components extending in a substantially perpendicular direction with respect to the plane of the plastic film to provide the flannel cloth-like texture; and feeding the split intermediate laminate structure from the exit side of the nip to a plurality of take-up rollers.

2. The method as claimed in claim 1, wherein a hot-melt adhesive is printed onto the layers of plastic film.

3. The method as claimed in claim 1, wherein a hot-melt adhesive is sprayed onto the layers of plastic film.

4. The method as claimed in claim 1, wherein a hot-melt adhesive is coated onto the layers of plastic film.

5. A method of making a flannelized film having a flannel cloth-like texture, comprising:

feeding a plurality of layers of co-extruded plastic film comprising a relatively thick layer and a relatively thin layer having a lower melt temperature than that of the thick layer between a plurality of heated rollers, the rollers meeting at a nip having a feed side and an exit side;

preheating the layers of plastic film to the softening point of the thin layer before the layers of plastic film reach the nip;

laminating a layer of creped tissue comprising a plurality of sinusoidal cellulosic fibers defining a nominal plane between the plurality of layers of plastic film, the sinusoidal fibers of said layer of creped tissue coming into contact with the surface of the preheated layers of plastic film to form an intermediate laminate structure;

splitting the intermediate laminate structure along the nominal plane of the creped tissue such that said sinusoidal fibers are split into a plurality of U-shaped fibers, a portion of the U-shaped fibers of the creped tissue having components extending in a substantially perpendicular direction with respect to the plane of the plastic film to provide the flannel cloth-like texture; and feeding the split intermediate laminate structure to a plurality of take-up rollers.

6. The method as claimed in claim 5, further comprising the step of forming apertures throughout the split intermediate laminate structure.

* * * * *